US006838420B2

(12) United States Patent
Sachdev

(10) Patent No.: US 6,838,420 B2
(45) Date of Patent: Jan. 4, 2005

(54) SOAP COMPOSITION

(75) Inventor: Amit Sachdev, Scotch Plains, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 10/364,044

(22) Filed: Feb. 11, 2003

(65) Prior Publication Data

US 2003/0166480 A1 Sep. 4, 2003

(51) Int. Cl.[7] .......... A61K 7/50

(52) U.S. Cl. .......... 510/141; 510/147; 510/152; 510/153; 510/155

(58) Field of Search .......... 510/141, 147, 510/152, 153, 155

(56) References Cited

U.S. PATENT DOCUMENTS

| | | | | |
|---|---|---|---|---|
| 4,290,904 | A | 9/1981 | Poper et al. | 252/118 |
| 4,303,543 | A | 12/1981 | Mansy | 252/117 |
| 4,758,370 | A | 7/1988 | Jungermann et al. | 252/132 |
| 5,041,234 | A | 8/1991 | Instone et al. | 252/118 |
| 5,310,495 | A | 5/1994 | Hill et al. | 252/118 |
| 5,417,876 | A | 5/1995 | Tokosh et al. | 252/108 |
| 5,529,714 | A | 6/1996 | Tokosh | 252/108 |
| 5,703,025 | A | 12/1997 | Zyngler et al. | 510/147 |
| 5,786,311 | A | 7/1998 | Zyngier et al. | 510/147 |
| 6,297,205 | B1 | 10/2001 | Saxena et al. | 510/141 |
| 6,310,015 | B1 | 10/2001 | Diez et al. | 510/130 |
| 6,395,692 | B1 | 5/2002 | Jaworska et al. | 510/147 |

FOREIGN PATENT DOCUMENTS

| | | |
|---|---|---|
| WO | WO 96/04360 | 2/1996 |
| WO | WO 98/14559 | 4/1998 |

*Primary Examiner*—Necholus Ogden

(57) ABSTRACT

A translucent or transparent composition comprising a. about 3 to about 40 wt. % soap, b. about 4 to about 40 wt. % of at least one synthetic surfactant, c. about 14 to about 45 wt. % water, d. from 0 to about 3 wt. % lower monohydric alcohol, e. about 5 to about 60 wt. % of a humectant, f. from 0 to about 5 wt. % of a structurant, g. from 0 to about 10 wt. % of a gellant with the proviso that the structurant and gellant are not 0 at the same time.

13 Claims, No Drawings

SOAP COMPOSITION

RELATED APPLICATIONS

This application claims the benefit of now abandoned provisional application 60/360,396 filed on Feb. 28, 2002.

BACKGROUND OF THE INVENTION

There have been many attempts to make a better soap containing bar that combines the beauty of transparency or translucency with an appropriate level of cleansing ability. Frequently, the concept of cleansing ability is associated with the quantity of lather obtained with the bar during the aqueous washing period. Such a bar should also be mild to the skin, have good rinsability and be able to deliver a fragrance to the bar user.

It has now been discovered that certain ranges and combination of soap, synthetic surfactant, water, lower monohydric alcohol, humectant, structurant and gellant can bring about an excellent combination of desirable characteristics.

SUMMARY OF THE INVENTION

In accordance with the composition, there is a translucent or transparent cleansing composition comprising a. about 3 to about 40 wt. % soap, b. about 4 to about 40 wt. % of at least one synthetic surfactant, c. about 14 to about 45 wt. % water, d. from 0 to about 3 wt. % lower monohydric alcohol, e. about 5 to about 60 wt. % of a humectant, f. from 0 to about 5 wt. % of a structurant, g. from 0 to about 10 wt. % of a gellant with the proviso that the structurant and gellant are not 0 at the same time.

DETAILED DESCRIPTION OF THE INVENTION

The soap bar components can bring about a combination of desirable characteristics such as better fragrance delivery when a fragrance is employed in the bar, improved mildness, and better rinsability. The bar is transparent or preferably translucent. By translucent is meant the visual perception of transmittance of any light through a ¼ inch thick portion of the bar. By transparency is meant the ability to read 14 point type though a quarter inch thick section of the bar.

The amount of soap, that is a long chain alkyl with some unsaturation possible, up to 20% of bonds as a carboxylic acid salt (sodium, potassium, ammonium or hydroxyethyl ammonium cations) is a minimum of about 3, 4, 5, 10 or 1 wt. % of the composition, and up to about 25, 30, 35 or 40 wt. % maximum of soap in the composition.

Other surfactants can be present in the composition as well. Examples of such surfactants are the anionic, amphoteric, nonionic and cationic surfactants. Examples of anionic surfactants include but are not limited to soaps, alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

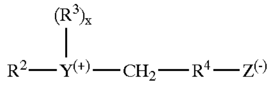

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-4-(N,N-di(2-hydroxyethyl)-N-(2 hydroxydodecyl) ammonio]-butane-1-carboxylate; 3-[S-ethyl-S-(3-dodecoxy-2-hydroxypropyl) sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate.

Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hyd roxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;

dodecyltrimethylammonium chloride;

nonylbenzylethyldimethyl ammonium nitrate;

tetradecylpyridinium bromide;

laurylpyridinium chloride;

cetylpyridinium chloride laurylpyridinium chloride;

laurylisoquinolium bromide;

ditallow(Hydrogenated)dimethyl ammonium chloride;

dilauryldimethyl ammonium chloride; and stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.
2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.
3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).
4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyidodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethyl-hexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyidimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyidi(2-hydroxyethyl)phosphine oxide, tetradecylmethyl-2-hydroxypropylphosphine oxide, oleyidimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

The quantity of synthetic surfactant in the bar composition, if present, is a minimum of about 2, 3, 4, 5, 7 or 9 wt. % and a maximum of about 40, 20 or 12 wt. % or even lower such as about 10 wt. %.

Water present in the bar composition is a minimum of about 14, 15 or 17 wt. % and a maximum of about 20, 25, 30, 35 or 45 wt. % of the bar composition.

Lower monohydric alkanols can also be present in the composition. Exemplary of lower monohydric alkanols are methanol, ethanol, propanol, isopropanol, and the like. The quantity of lower monohydric alkanol present in the composition is a minimum of 0, about 0.1 or 0.2 wt. %. The maximum quantity is about 3, 2, or 1 wt. %.

A humectant is a polyhydric alcohol organic material which assists in solubilizing soap. Exemplary of these materials is propylene glycol, dipropylene glycol, glycerin, sorbitol, mannitol, xylitol, hexylene glycol, and the like. A minimum of humectant in the composition is about 5, 8, 10, 15 or 20 wt. %. A maximum is about 60, 50, 40, or 30 wt. % of the composition.

A structurant, a material that makes the bar harder can be present in the composition. Exemplary of a structurant is alkali halides and alkali metal sulfates such as sodium chloride and sodium sulfate. Levels of structurant are 0 or at least about 0.1 or 0.2 wt. % of the bar. Maximum quantities of structurant are about 5, 4, 3, 2 or 1 wt. %. It is preferable that the structurant be above 0.

Also present in the composition can be a gellant which is generally a nonionic or polymeric agent which assists in hardening the bar. Exemplary of gellants is guar gums, polyamides, and the like. Quantities of gellant can be 0 or at least 0.1, 0.2, 0.3 or 0.5 wt. %. Maximum quantities of gellant are about 5, 2 or 1 wt. %. Neither the gellant nor the structurant should be zero at the same time. The gellant is preferably about zero.

Optional ingredients which can be present in the composition include fragrance, dyes, chelating agents such as EDTA, antimicrobial materials such as triclocarban, triclosan and the like, preservatives such as hydantoins, imidazolines and the like. The fragrance can be absent or be present at about 0.001 to about 2 wt. % of the composition. The fragrance can include any active agent such as a phenolic, aldehyde, alcohol, nitrile, ether, ketone or ester and the like.

When the fragrance is present in the composition, the lower monohydric alcohol can enhance the delivery of the fragrance to the soap bar user. With its volatility, the alcohol assists in making the user aware and appreciative of the fragrance.

The presence of the synthetic surfactant brings about good lathering and feel to the skin. Preferred surfactants are acyl isethionates, alkyl ether sulfates and alkyl sulfosuccinates. Rinsability is also enhanced with the total composition components.

The bars are prepared by standard procedures. The translucent bars are prepared by pressing (molding) or pouring (cast) methodologies, i.e., placing a liquid into a mold. The transparent bars are generally prepared by pouring (casting) procedures.

Below are example(s) of the invention.

| Example 1 | Wt. % | Example 2 | Wt. % |
|---|---|---|---|
| Propylene Glycol | 12 | Propylene Glycol | 16 |
| Glycerin | 5 | Glycerin | 6 |
| Sorbitol | 7 | Dipropylene Glycol | 4 |
| Sodium Laureth Sulfate | 12 | Sodium Laureth Sulfate | 10 |
| Cocoamido Propyl Betaine | 2 | Sodium Cocoyl Isethionate | 5 |
| | | Cocoamido Propyl Betaine | 3 |
| Disodium Lauryl Sulfosuccinate | 8 | Sodium Chloride | 2 |
| | | Stearic Acid | 10 |
| Sodium Chloride | 1.5 | Myristic Acid | 5.0 |
| Stearic Acid | 9.5 | Coconut Acid | 3.0 |
| Myristic Acid | 4.2 | Sodium Hydroxide | 5.6 |
| Coconut Acid | 3.2 | Sucrose | 2.0 |
| Sodium Hydroxide | 5.5 | Ethanol | 1.5 |
| Sucrose | 2.0 | Fragrance | 1.0 |
| Triethanolamine | 1.5 | Water | 25.9 |
| Ethanol | 0.5 | | |
| Fragrance | 1.0 | | |
| Water | 25.1 | | |

A further preferred composition has the following ranges and provides a solid composition, preferably a bar, which is translucent.

| Component | wt % |
|---|---|
| Soap | 10–30 |
| Synthetic Surfactant | 15–25 |
| Water | 15–25 |
| Monohydric alcohol | 0.20–1 |
| Humectant | 15–30 |
| Structuant | 0.5–1.5 |
| Gellant | 0–3 |
| Water | QS |

Generally, the soap is comprised of soluble salts of stearate, myristate, and cocoate. Translucency is enhanced by using ratios of stearate: myristate (longer chain to shorter chain) of about 1.5 to 3.5:1, preferably about 1.6 to 2.25:1.

Skin conditioning can be achieved while maintaining the translucency of the composition. For example, various fats and oils can be used for increased skin feel. Examples include soybean oil, sunflower oil, canola oil, various unsaturated long chain oils and fats in general, shea butter and the like. Quantities of these fats and oils can be a minimum that provides a skin feel up to a maximum that provides skin feel while still achieving translucency of the composition. Generally, this is about 0.5 to about 4 wt % of the composition preferably about 1.0 to about 3.0 wt %.

Other emollients can also be in the composition. Examples of these materials include silicone quats such as silicone quaternium-8, and the like;lanolin quats such as Quarternium 33 and cationic polymers such as polyquat-6 and polyquat-7. Additionally, lather affecting reagents such as polyethylene oxide (Polyox®) from Union Carbide can also be employed.

These materials can be used at relatively minor quantities that are from about 0.05 to about 3 to 4 wt % of each of these as long as skin feel and translucency is maintained. Mixtures of conditioning agents can be used. Below are various emollients, fats and oils, as in general skin conditioning agents, which maintained translucency and provided skin feel when added to a translucent composition of the invention at a level of 2 wt. %.

Fats and Oils

Soybean oil
Sunflower seed oil
Meadowfoam seed oil
Shea butter
Mineral oil

Emollients

Di-PPG-2 myreth-10 adipate
Glycereth-7 lactate
IPDI/PEG-15 cocamine copolymer
Propylene glycol isostearate
PEG-75 meadowfoam oil
PPG-3 hydroxyethyl soyamide
Acetylated lanolin alcohol
C12–15 alkyl benzoate
PEG-6 caprylic/capric glycerides
PEG-7 glyceryl cocoate
Lanolin quat (quaternium-33)
Silicone quaternium-8
Quaternized hydrogenated wheat protein Quats Polyquaternium-7
Polyquaternium-6
Polyquaternium-44

Hydrocarbons

Petrolatum
PEG-45M (polyox WSR N60K)

Mixtures of two or more of these emollients can be used.

A preferred skin composition is shown below:

| Component | Wt. |
|---|---|
| Water | QS |
| Propylene glycol | 16 |
| Dipropylene glycol | 6 |
| Cocoamidopropyl betaine | 7 |
| Sodium chloride | 1 |
| Stearic acid | 14 |
| Myristic acid | 7.3 |
| Coconut acid | 6.23 |
| Caustic soda (50%) | 8.54 |
| SD Alcohol 3-C | 0.2 |
| Sodium laureth sulfate | 12 |
| Cocamide MEA | 1 |
| Disodium lauryl sulfosuccinate | 4.5 |
| Sodium lauryl sulfate | 4 |
| Sucrose | 4 |
| Soybean oil | 2.5 |
| Lanolin quat | 1 |
| Polyquat-6 (28%) | 0.7 |
| Fragrance and minors | 1.5 |

Below are the results on clarity and bar hardness (penetration of a needle under controlled conditions) the lower the number the harder and more preferred the bar.

| Soap Ratios | | | | | |
|---|---|---|---|---|---|
| Sodium Stearate | Sodium Myristate | Sodium Cocoate | Stearate/ Myristate | Clarity | Bar Hardness (mm) |
| 13 | 5 | 6 | 2.6 | Translucent | 7.45 |
| 13 | 0 | 11 | — | Opaque | 8.07 |
| 13 | 2 | 9 | 6.5 | Opaque | 7.18 |
| 13 | 4 | 7 | 3.25 | Translucent | 5.85 |
| 13 | 8 | 3 | 1.6 | Transparent | 5.45 |

The following base formula is used in sensory panel evaluation:

| Component | Wt. |
|---|---|
| Water | QS |
| Propylene glycol | 16 |
| Dipropylene glycol | 8 |
| Cocoamidopropyl betaine | 7 |
| Sodium chloride | 1 |
| Stearic acid | 12 |
| Myristic acid | 4.56 |
| Coconut acid | 8.95 |
| Caustic Soda (50%) | 7.9 |
| SD Alcohol 3-C | 0.2 |
| Sodium laureth sulfate | 11 |
| Cocamide MEA | 1 |
| Disodium lauryl solfosuccinate | 4.5 |
| Sodium lauryl sulfate | 4 |
| Sucrose | 3 |
| Fragrance and minors | 1.5 |

To one portion of the formula is added 2 wt. % soybean oil and 1 wt. % quaternium-33. To a second portion of the formula is added 1 wt. % quaternium-33 and 1 wt. % petrolatum. To a third portion of the formula is added 1 wt % petrolatum and 1 wt. % silicone quaternium-8. The formulas are then evaluated. Quaternium-33 alone or in combination with another conditioning agent is preferred.

What is claimed is:

1. A translucent or transparent composition comprising a. about 3 to about 40 wt. % soap, b. about 4 to about 40 wt. % of at least one synthetic surfactant, c. about 14 to about 45 wt. % water, d. from 0.1 to about 3 wt. % of a lower monohydric alcohol, e. about 5 to about 60 wt. % of a humectant, f. from 0 to about 5 wt. % of a structurant, g. from 0 to about 10 wt. % of a gellant, provided that the structurant and gellant are not 0 at the same time.

2. The composition in accordance with claim 1 wherein soap is about 4 to about 35 wt. %.

3. The composition in accordance with claim 1 wherein soap is about 15 to about 35 wt. %.

4. The composition in accordance with claim 1 wherein it is a bar.

5. The composition in accordance with claim 1 wherein th soap (a) is a long chain alkyl optionally with some unsaturation having up to 20% of bonds as a carboxylic acid; and (b) comprises a cation selected from the group consisting of sodium, potassium, ammonium and hydroxyethyl ammonium.

6. The composition in accordance with claim 1 wherein th synthetic surfactant is an anionic surfactant selected from the group consisting of alkyl sulfates, anionic acyl sarcosinates, methyl acyl taurates N-acyl glutamates, acyl isethionates, alkyl ether sulfates, alkyl sulfosuccinates, alkyl phosphate esters, ethoxylated alkyl phosphate esters, trideceth sulfates, and mixtures of ethoxylated alkyl sulfates, wherein the alkyl chains for the synthetic surfactants are $C_8$–$C_{22}$ alkyls.

7. The composition in accordance with claim 1 wherein th synthetic surfactant is an anionic non-soap surfactant selected from th group consisting of alkali metal salts of organic sulfate comprising in their molecular structure an alkyl radical containing from about 8 t about 22 carbon atoms, a sulfonic acid or a sulfuric acid ester radical.

8. The composition in accordance with claim 1 wherein th synthetic surfactant is a zwitterionic surfactant of formula

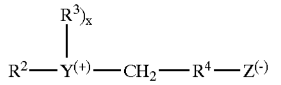

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is a alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms, and Z is a radical selected from the group consisting of carboxylate, sulfonate, sulfate, phosphonate, and phosphate groups.

9. The composition in accordance with claim 1 wherein th synthetic surfactant is a zwitterionic surfactant selected from the group consisting of 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

10. The composition in accordance with claim 1 wherein th synthetic surfactant is an amphoteric surfactant selected from the group consisting of derivatives of aliphatic secondary and tertiary amines in which the aliphatic radical can be straight chain or branched and wherein one of the aliphatic substituents contains from about 8 to about 18 carbon atoms and one of the aliphatic substituents contains an anionic water solubilizing group selected from the group consisting of carboxy, sulfonate, sulfate, phosphate, and phosphonate.

11. The composition in accordance with claim 1 wherein th synthetic surfactant is an amphoteric surfactant which is a betaine selected from the group consisting of coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl, oleyl dimethyl gamma-carboxypropyl betaine, lauryl bis-(2-hydro-xypropyl) alpha-carboxyethyl betaine, coco dimethyl sulfopropyl betaine, stearyl dimethyl sulfopropyl betaine, amido betaines, and amidosulfobetaines.

12. The composition in accordance with claim 1 wherein the synthetic surfactant is a cationic surfactant selected from the group consisting of stearyldimenthylbenzyl ammonium chloride;

dodecyltrimethylammonium chloride;

nonylbenzylethyldimethyl ammonium nitrate;

tetradecylpyridinium bromide;

laurylpyridinium chloride;

cetylpyridinium chloride;

laurylpyridinium chloride;

laurylisoquinolium bromide;

ditallow(Hydrogenated)dimethyl ammonium chloride;

dilauryldimethyl ammonium chloride; and stearalkonium chloride.

13. The composition in accordance with claim 1 wherein the synthetic surfactant is a nonionic surfactant selected from the group consisting of:

(a) polyethylene oxide condensates of alkyl phenols which are condensation products of alkyl phenols having an alkyl group containing from about 6 to 12 carbon atoms in either a straight chain or ranched chain configuration, with ethylene oxide, the said ethylene oxide being present in amounts equal to 10 to 60 moles of ethylene oxide per mole of alkyl phenol;

(b) products which are derived from ethylene oxide with a product resulting from the reaction of propylene oxide and ethylene diamine selected from the group consisting of compounds containing from about 40% to about 80% polyoxyethylene by weight and having a molecular weight of from about 5,000 to about 11,000 resulting from th reaction of ethylene oxide groups with a hydrophobic base constituted of a reaction product of ethylene diamine and excess propylene oxide, said base having a molecular weight of the order of 2,500 to 3,000;

(c) condensation products of aliphatic alcohols having from 8 to 18 carbon atoms, in either straight chain or branched chain configuration with ethylene oxide;

(d) long chain tertiary amine oxides corresponding to formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ a $R_3$ contain from 1 to about 3 carbon atoms and from 0 to about 1 hydroxy group;

(e) long chain tertiary phosphine oxides corresponding to formula:

$$RR'R''P \rightarrow O$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms;

(f) long chain dialkyl sulfoxides containing one short chain alkyl or hydroxy alkyl radical of 1 to about 3 carbon atoms and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety; and (g) alkylated polyglycosides wherein the alkyl group is from about 8 to about 20 carbon atoms and the degree of polymerization of the glycoside is from about 1 to about 3.

* * * * *